(12) United States Patent
Gaddum

(10) Patent No.: US 9,021,889 B2
(45) Date of Patent: May 5, 2015

(54) SAMPLE HOLDER FOR RECEIVING A SAMPLE

(75) Inventor: Ronald R. Gaddum, Ahlden/Aller (DE)

(73) Assignee: Gabo Qualimeter Testanlagen GMBH, Ahlden (DE)

( * ) Notice: Subject to any disclaimer, the term of this patent is extended or adjusted under 35 U.S.C. 154(b) by 170 days.

(21) Appl. No.: 13/989,013

(22) PCT Filed: Nov. 22, 2011

(86) PCT No.: PCT/EP2011/070653
§ 371 (c)(1),
(2), (4) Date: Aug. 14, 2013

(87) PCT Pub. No.: WO2012/069459
PCT Pub. Date: May 31, 2012

(65) Prior Publication Data
US 2014/0053656 A1    Feb. 27, 2014

(30) Foreign Application Priority Data

Nov. 22, 2010    (DE) .......................... 10 2010 061 742

(51) Int. Cl.
*G01N 3/02*    (2006.01)
*G01N 1/00*    (2006.01)
*G01N 3/04*    (2006.01)

(52) U.S. Cl.
CPC .. *G01N 1/00* (2013.01); *G01N 3/04* (2013.01); *G01N 2203/0206* (2013.01); *G01N 2203/0447* (2013.01); *G01N 3/02* (2013.01)

(58) Field of Classification Search
CPC .............. G01N 2203/0206; G01N 2203/0447; G11C 27/02
USPC ........................................ 73/760, 856, 866.5
See application file for complete search history.

(56) References Cited

U.S. PATENT DOCUMENTS

| | | | |
|---|---|---|---|
| 2,587,226 A | 2/1952 | Rodman | |
| 3,885,424 A | 5/1975 | Ryckman et al. | |
| 4,431,276 A * | 2/1984 | Weber | 359/503 |
| 4,490,025 A * | 12/1984 | Weber et al. | 359/391 |
| 4,606,230 A | 8/1986 | Scott et al. | |
| 5,225,683 A * | 7/1993 | Suzuki et al. | 250/442.11 |
| 6,395,554 B1 * | 5/2002 | Regan et al. | 436/46 |
| 6,399,026 B1 * | 6/2002 | Karrai | 422/561 |
| 2001/0007640 A1 * | 7/2001 | Edwards et al. | 422/63 |

(Continued)

FOREIGN PATENT DOCUMENTS

| | | |
|---|---|---|
| CN | 201188077 Y | 1/2009 |
| CN | 201215537 Y | 4/2009 |
| DE | EP0750171 A2 | 12/1996 |
| DE | 69724021 T2 | 6/2004 |

(Continued)

OTHER PUBLICATIONS

PCT Internaltion Publication and International Search Report for PCT/EP2011/07653 "Sample Holder for Receiving a Sample", filed Nov. 22, 2011, 31 pages.

*Primary Examiner* — Max Noori
(74) *Attorney, Agent, or Firm* — Lee & Hayes, PLLC

(57) ABSTRACT

A sample holder for receiving a sample includes a sample receiving device for clamping the sample, which is assigned a holding means which has at least two prongs protruding from the sample receiving device for a gripping means. Also disclosed are a receiving device, a sample holder magazine, a sample feeding system, a clamping device and an examining device.

13 Claims, 3 Drawing Sheets

(56) References Cited

U.S. PATENT DOCUMENTS

2004/0169510 A1* 9/2004 Fields et al. .................. 324/262
2004/0211899 A1* 10/2004 Ezumi et al. .................. 250/310

FOREIGN PATENT DOCUMENTS

DE 102009010431 A1 9/2010
WO WO2009139795 A1 11/2009

* cited by examiner

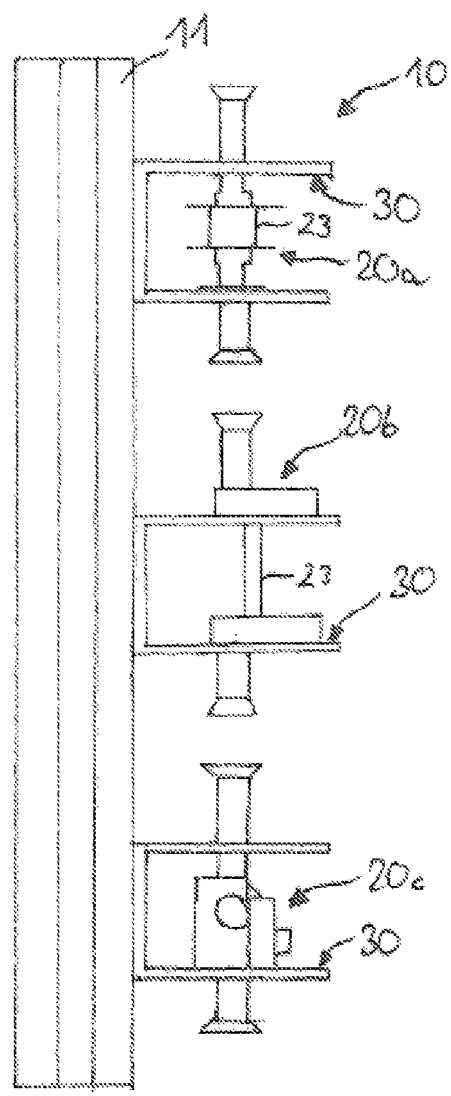
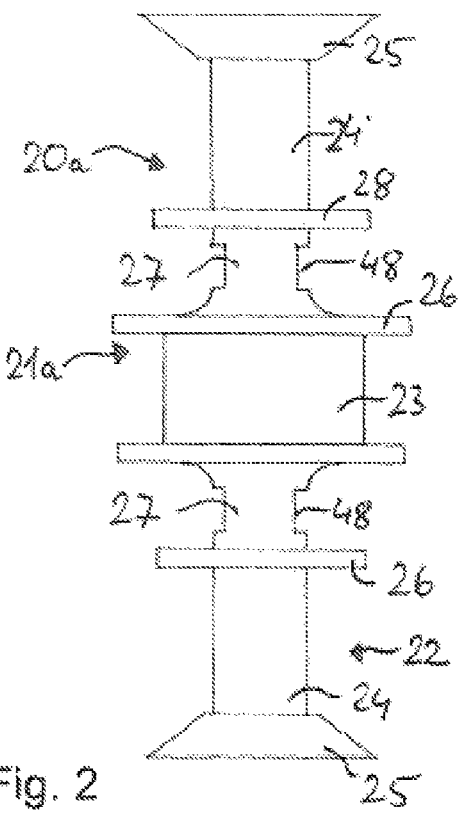
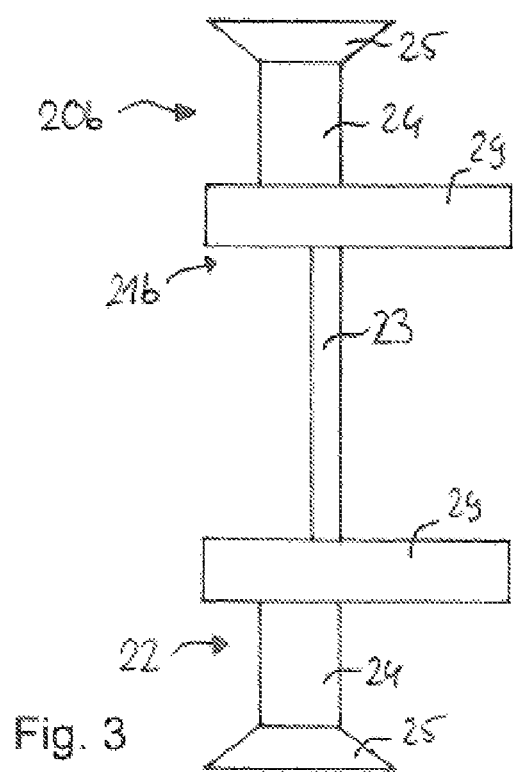
Fig. 1
Fig. 2
Fig. 3

SAMPLE HOLDER FOR RECEIVING A SAMPLE

This application is a 35 U.S.C. 371 National Stage Entry of and claims priority to PCT Application Serial No. PCT/EP2011/070653, entitled "Sample Holder For Receiving a Sample," filed on Nov. 22, 2011, and German Patent Application No. 10 2010 061 742.3, entitled "Sample Holder For Receiving a Sample," filed on Nov. 22, 2010, both of which are fully incorporated by reference herein.

The invention relates to a specimen holder for mounting a specimen, in particular for spectroscopic materials testing. The invention further relates to a mounting device for mounting a specimen holder according to the invention. Furthermore, the invention relates to a specimen holder magazine, a specimen feed system, a clamping device and a test unit for such a specimen holder.

Spectroscopic materials testing is a method used in dynamic mechanical spectroscopy (DMTS, DMTA, DMA) for testing a wide range of materials. Here, the specimen is exposed—free of preload or under static load—to sinusoidal mechanical excitations at testing frequencies of 0.0001 Hz to 1,000 Hz. Based on the time gaps between impulse and specimen response, the visco-elastic properties of the specimen material, which provide important indications of the quality of the product, can be established. The specimens can be exposed to tensile, compressive, bending and shear force.

The DMTS method is applied both in the field of research and development and also in the field of in quality control. By means of DIMS, the dynamic properties of a wide range of materials, such as elastomers, polymers, composite materials, metals, glass, ceramic materials, biomaterials, foodstuffs, adhesives, plastic materials and fluids, can be established.

For testing, the specimen material has to be fed to a test unit. The feeding of the specimen material to the test unit is carried out by means of a so-called specimen feed system. A known specimen feed system has a specimen magazine for accommodating the specimens and a gripping system. The gripping system removes a specimen from the specimen magazine and feeds the former to a clamping device which is located in the test unit. A specimen holder, which holds the specimen for testing, is clamped in the clamping device itself. Depending on the type of test, i.e. a tensile, bending, shear or compression test, a corresponding specimen holder is required. Following the measurement, the specimen material is removed again from the test unit.

It is disadvantageous in this context that it is to date only possible for one type of congeneric specimens, i.e. tensile, compression, bending or shear specimens, to be inserted into the test unit, measured and subsequently removed in succession. Accordingly, the specimen magazine has to be changed for testing another type of specimens. It may further be necessary to clean or exchange the specimen holders in the event that it has been soiled during a test.

The object of the present invention is to improve the devices of the aforementioned type in such a manner that specimens of diverse geometry and load types (tensile, compressive, bending and shear) can be automatically placed into, measured in and removed again from the test unit in succession.

The object is achieved according to the invention by proposing a specimen holder having the characteristics of claim 1, a mounting device as claimed in claim 4, a specimen holder magazine as claimed in claim 10, a specimen feed system with the characteristics of claim 11, a clamping device as claimed in claim 14 and a test unit as claimed in claim 15.

The specimen holder according to the invention for mounting a specimen has a specimen mounting device for clamping the specimen, a holding means being assigned to said specimen mounting device, said holding means having at least two pegs, which protrude from the specimen mounting device, for a gripping means. The specimen holder according to the invention has two pegs which protrude from the specimen mounting device, a gripping system being capable of finding grip on said pegs by means of its gripping pliers and thus being able to feed the specimen, which is already clamped in the, as a complete unit to a test unit and remove it from there again. Accordingly, it is possible to feed specimens of different geometries and load types (tensile, compressive, bending and shear) to the test unit and to remove them from there again. This enables specimens of different geometries and load types to be placed into the test unit in any sequence. Since the specimen holder with the specimens inserted therein is removed after every measurement and a new specimen holder complete with specimen is inserted, the risk of soiling, in particular in the context of measuring the green adhesion of vulcanized rubber, is reduced.

In an advantageous embodiment, the pegs have an approximately conically shaped end region. The conically shaped end region serves to clamp the specimen holder in the clamping device of the test unit.

The pegs advantageously protrude perpendicularly from opposite sides of the specimen mounting device. This ensures that the specimens are not already mechanically stressed during transport by the specimen holder's own weight.

The invention further relates to a mounting device for mounting a specimen holder according to the invention having a recess, which is formed into the mounting device, for mounting the holding means of the specimen holder. Specimen holders with specimens of different geometries and load types can be mounted on the mounting device.

The mounting device advantageously has a first mounting angle and a second mounting angle, each mounting angle having an approximately L-shaped cross section with a first leg and a second leg.

A recess is advantageously formed into each of the first legs of the mounting angles. Accordingly, both pegs which protrude from the specimen mounting device are mounted on the mounting device.

In an advantageous embodiment, the recesses are surrounded by a first depression. The first mounting angle advantageously has a second depression which is formed into the first depression. The first depression here is advantageously configured approximately rectangular and the second depression is configured approximately circular for the form-fitting mounting of a specimen mounting device. The specimen mounting device sits in the depressions, such that the specimen is not mechanically stressed by the specimen holder's own weight and does not tend to creep. In consequence, thin film specimens, but also fibers, strips of rubber, hard plastics, composite materials or also metals can be clamped in a specimen holder and placed on the mounting device. Furthermore, a secure mounting of the specimen holders within the mounting device is ensured by the depressions.

The invention further relates to a specimen holder magazine for accommodating a plurality of specimen holders according to the invention. The specimen holder magazine has a carrier stand and at least one mounting device according to the invention which is fastened on the carrier stand. The specimen holder magazine is distinguished in that specimens having different geometries and shapes and clamped in specimen holders are arrangeable as a complete unit on the specimen holder magazine, the complete unit being fed to the test unit. Accordingly, specimens having different geometries and shapes can be placed into the test unit in any sequence.

The invention further relates to a specimen feed system for feeding specimen holders according to the invention to a test unit, having a specimen holder according to the invention and a gripping system which grips the specimen holders on the holding means and feeds them to a clamping device which is located in the test unit.

In an advantageous embodiment, the gripping system has two gripping pliers at a distance from one another which grip the holding means of the specimen holder.

In a further advantageous embodiment, the gripping system is pivotable about its longitudinal axis.

Furthermore, the invention relates to a clamping device for mounting a specimen holder according to the invention on the holding means, the clamping device is located in a test unit for spectroscopic materials testing.

The invention further relates to a test unit for spectroscopic materials testing having a specimen feed system according to the invention and a clamping device according to the invention.

The invention is explained in more detail in the following by means of exemplary embodiments which are schematically illustrated in the drawings, in which:

FIG. 1 is a lateral view of a specimen holder magazine according to the invention having arranged thereon specimen holders according to the invention for specimens of different geometries and load types;

FIG. 2 is a schematic illustration of a specimen holder according to the invention with a clamped compressive test specimen;

FIG. 3 is a schematic illustration of a specimen holder according to the invention according to a second embodiment with a clamped tensile test specimen;

Figures 4, 5:
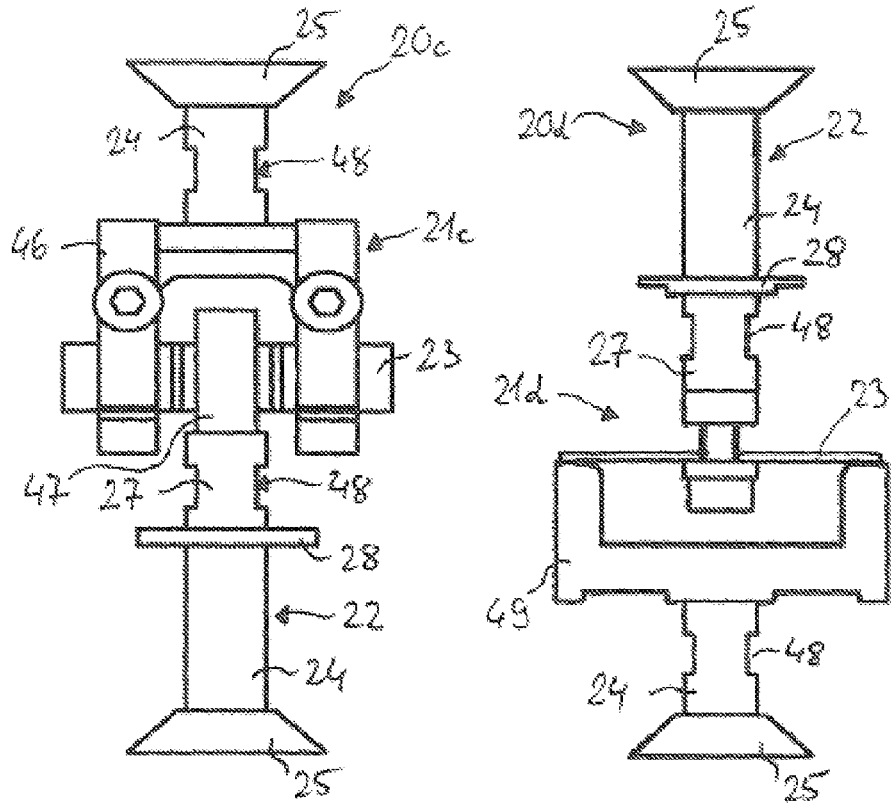
FIG. 4 is a schematic illustration of a specimen holder according to the invention according to a third embodiment with a clamped shear test specimen.
FIG. 5 is a schematic illustration of a specimen holder according to the invention according to a fourth embodiment with a clamped bending test specimen.

FIG. 1 shows a specimen holder magazine 10 for accommodating a plurality of different specimen holders 20. The specimen holders 20 serve as mounting for a specimen 23 for spectroscopic materials testing.

The specimen holder magazine 10 has a carrier stand 11 and multiple mounting devices 30, which are arranged on the carrier stand 11, for the form-fitting mounting of the specimen holders 20. The mounting devices 30 are fastened on the carrier stand 11. Three different specimen holders 20 are fastened on the specimen holder magazine 10, namely a specimen holder 20a for the compressive test, a specimen holder 20b for the tensile test and a specimen holder 20c for the shear test. Furthermore, a specimen holder 20d, which is not illustrated in FIG. 1, for the bending test is fastenable on the specimen holder magazine 10.

The specimen holders 20 for different load types are shown in more detail in FIGS. 2 to 5.

FIG. 2 shows a specimen holder 20a for a compressive test. The specimen holder 20a has a specimen mounting device 21a and a holding means 22. A specimen 23 for the compressive test is clamped in the specimen mounting device 21a, a variety of specimen materials being mountable. The specimen mounting device 21a has two holding plates 26, the specimen 23 being mounted in between. A transitional region 27 having constrictions 48 which are formed therein adjoins each holding plate 26, said constrictions serving as key surfaces for the assembly. A plate 28 is adjacent to each transitional region 27, the holding means 22 adjoining the topsides of the plates 28. The holding means 22 has two pegs 24 which perpendicularly protrude from the plates 28. The pegs 24 have a conically shaped end region 25. For the compressive test, the specimen 23 is positively positioned by being glued to the two holding plates 26.

FIG. 3 shows a specimen holder 20b for a tensile test. The specimen holder 20b has a specimen mounting device 21b and the holding means 22. The specimen mounting device 21b has two clamping jaws 29. As is evident in FIG. 3, a specimen 23 is clamped at each of its ends in the clamping jaws 29. The holding means 22 adjoins the topside of the clamping jaws 29. The holding means 22 has two pegs 24 which protrude perpendicularly from the topside of the clamping jaws 29. The pegs 24 have a conically shaped end region 25.

A specimen holder 20c for a shear test is shown in FIG. 4. The specimen holder 20c has a specimen mounting device 21c and the holding means 22. A specimen 23 is clamped in the specimen mounting device 21c. The specimen mounting device 21c has a holder 46 which is formed approximately in a U-shape. As is evident in FIG. 4, the specimen 23 is clamped at each of its ends on legs of the holder 46. The specimen mounting device 21c further has a clamping jaw 47 which is located between the legs of the holder 46 and also clamps the specimen 23. A transitional region 27 having a constriction 48 adjoins the clamping jaw 47, a plate being located on the transitional region 27. The holding means 22 adjoins the topside of the holder 46 and the topside of the plate 28. The holding means 22 has two perpendicularly protruding pegs 24 which have a conically shaped end region 25. A constriction 48 is also formed into the peg 24 which protrudes from the holder 46. The constrictions 48 serve as a key surface for the assembly.

FIG. 5 shows a specimen holder 20d for a bending test. The specimen holder 20d has a specimen mounting device 22d and the holding means 22. The specimen mounting device 22d accommodates a specimen 23. For this purpose, the specimen mounting device 22d has an approximately U-shaped bearing 49, a stamp 50 and a support plate 51. Recesses 53 are formed into the bearing 49 for the form-fitting mesh with the mounting device 30. The stamp 50 and the support plate 51 are connected to one another at each end by two springs 52 in such a manner that a free space remains between stamp 50 and support plate 51. The specimen 23 is located between the stamp 50 and the support plate 51 in such a manner that the specimen 23 lies on legs of the bearing 49 and on the support plate 51, as shown in FIG. 5. A transitional region 27 having a constriction 48 formed therein adjoins the stamp 50. The transitional region 27 is delimited by a plate 28. The holding means 22 adjoins the plate 28 and the bearing 49. The holding means 22 comprises two perpendicularly protruding pegs 24 which each at their ends have a conically shaped end region 25. A constriction 48, which serve as a key surface for the assembly, is also formed into the pegs 24 which protrude from the holder 46.

Figure 6:
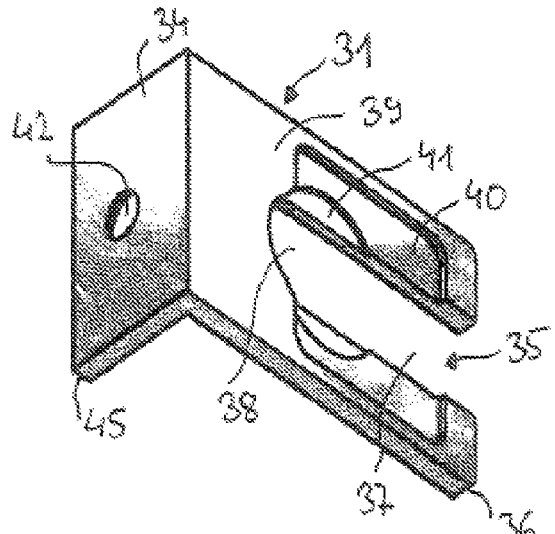
FIG. 6 is a perspective view of a first leg of a mounting device according to the invention.
Figure 7:
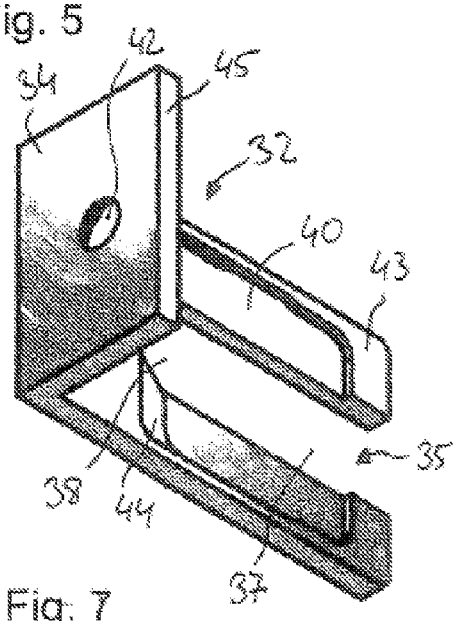
FIG. 7 is a perspective view of a second leg of a mounting device according to the invention.

As is evident in FIG. 1 and FIGS. 6 and 7, the mounting device 30 has a first mounting angle 31 and a second mounting angle 32. Both mounting angles 31, 32 each have a first leg 33 and a second leg 34, such that the two mounting angles 31, 32 have an approximately L-shaped cross section.

As is evident in FIG. 6, a recess 35 is formed into the first leg 33 of the first mounting angle 31. The recess 35 extends from an end side 36 of the first leg 33 in the direction of the second leg 34. The recess 35 has an oblong section 37 and a circular section 38. A first depression 40 is formed into an outside 39 of the first leg 33. The first depression 40 has a rectangular outline. Furthermore, a second depression 41 is formed into the first depression 40 and in the region of the circular section 38. In the second leg 34, an opening 42 for the leadthrough of a fastening means, which is not illustrated in more detail, is formed. By means of the opening 42, the first mounting angle 31 is fastenable on the carrier stand 11.

According to FIG. 7, the second mounting angle 32 has a first leg 33 and a second leg 34. The recess 35 is formed into the first leg 33 of the second mounting angle 32. The recess 35 likewise has the oblong section 37 and the circular section 38. Furthermore, the first depression 40 is formed on an inside 43 of the first leg 33. The first depression 40 of the second mounting angle 20 has an approximately rectangular basic shape, wherein in the direction of the second leg 34, the depression merges into an incline. There is formed into the second leg 34 an opening 42 for the leadthrough of a fastening means, which is not illustrated in more detail, for fastening the second mounting angle 32 on the carrier stand 11.

As is evident in FIG. 1, the two mounting angles 31, 32 are arranged on the carrier stand 11 such that end faces 45 of the second legs 34 are in contact with one another and the mounting device 30 forms approximately a U-shaped cross section.

Figure 8:
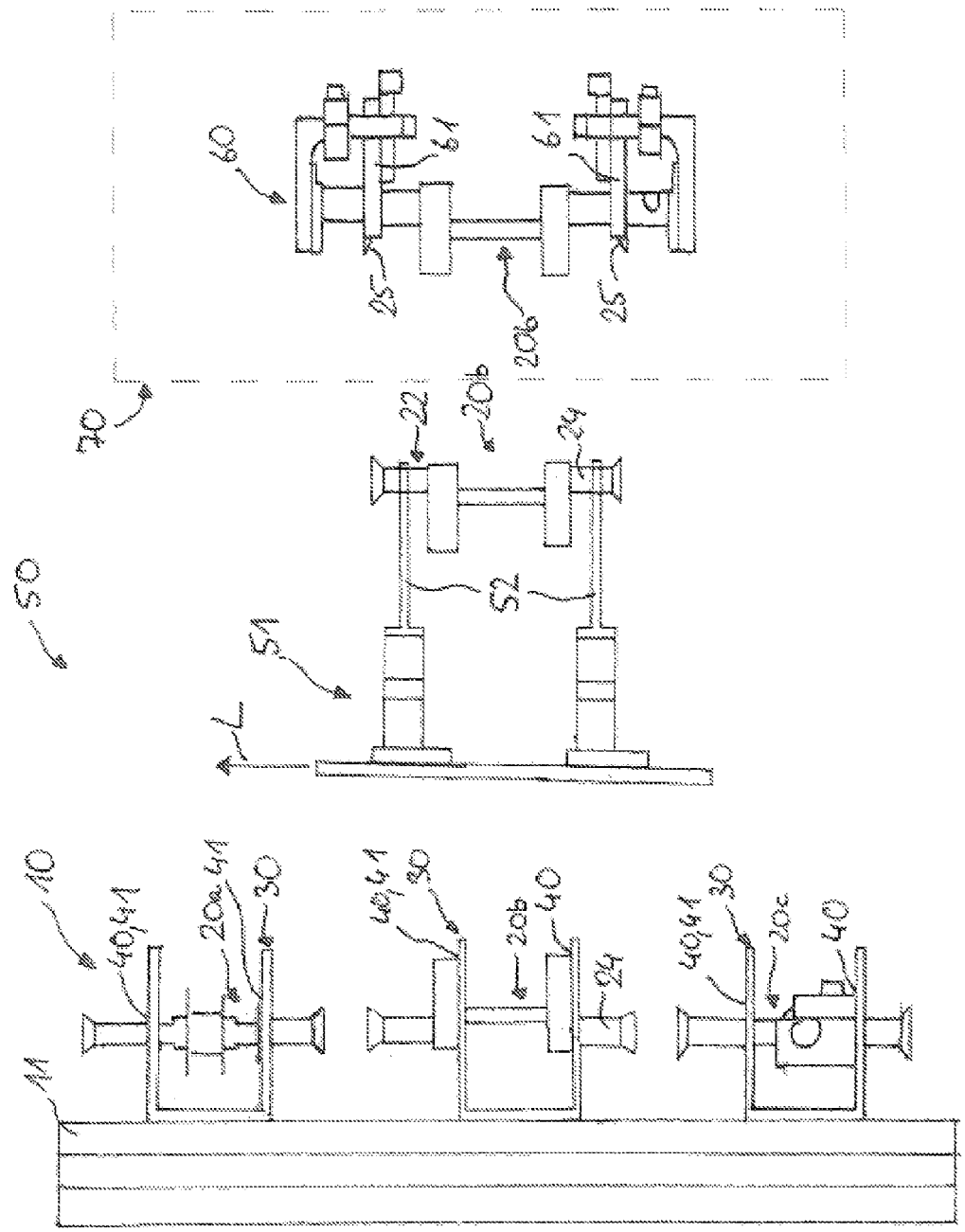
FIG. 8 is a schematic lateral view of a specimen feed system according to the invention and of a clamping device according to the invention which is located in a test unit.

In FIG. 8, a specimen feed system 50 is illustrated. The specimen feed system has the specimen holder magazine 10 having specimen holders 20 for different specimen types according to FIGS. 2 to 5 arranged thereon, and a gripping system 51. The gripping system 51 has two gripping pliers 52 at a distance from one another for gripping the holding means 22. The gripping system 51 is pivotable about a longitudinal axis L. The gripping pliers 52, which are located on the gripping system 51, are controllable mechanically, electro-mechanically or hydraulically.

FIG. 8 schematically shows a test unit 70 for dynamic mechanical spectroscopy. A clamping device 60 for mounting the specimen holders 20 is located inside the test unit 70. The clamping device 60 has pivotable clamping means 61 for clamping the specimen holders 20, said clamping means clamping the specimen holders 20 at their holding means 22, in particular at the conically shaped end regions 25. The operation of the clamping means 61 may be mechanical, electro-mechanical or hydraulic.

In the following, the mounting of the specimen holder 20 in the mounting device 30 is explained. The recess 35 of the mounting device 30 serves to introduce the pegs 24 into the mounting device 30. The pegs 24 are pushed into the recess 35 in the direction of the second leg 34 until the specimen mounting devices 21 and/or the plates 28 mesh in a form-fitting manner with the first depression 40 and/or the second depression 41. In the case of the specimen holder 20a, the plates 28 lie in a form-fitting manner in the second depressions 41 of the first mounting angle 31 and in the first depression 40 of the second mounting angle 32. The specimen mounting device 21b of the specimen holder 20b meshes in a form-fitting manner with the first depressions 40. In the case of the specimen holder 20c, the plate 28 lies in the second depression 41 of the first mounting angle 31 and the holder 46 lies in the first depression 40 of the second mounting angle 32. In the case of the specimen holder 20d, the plate 28 lies in a form-fitting manner in the second depression 41 of the first mounting angle 31, and the bearing 49 meshes with its recesses 53 in a form-fitting manner with the first leg 33 of the second mounting angle 32.

In the following, the feed of a specimen holder 20 to the clamping device 60, which is located in the test unit, and the removal of the specimen holder 20 from the clamping device 60 is explained in more detail. The gripping system 51 positions itself in front of the specimen holder 20 in such a manner that the gripping pliers 52 can grip the holding means 22, in particular the pegs 24. Once the gripping pliers 52 have gripped the pegs 24, the gripping system 51 slightly elevates the specimen holder 20 by means of a movement of the gripping system 51 in the direction of the indicated longitudinal axis L. This causes the removal of the specimen mounting device 21 from the depressions 40, 41. Subsequently, the gripping system 51 together with the specimen holder 20 moves in the horizontal direction away from the mounting device 30. Thereafter, the gripping system 51 pivots about its longitudinal axis L by approximately 270°, in order to feed the specimen holder 20 to the clamping device 60 which is located in the test unit 70. After the pivoting operation, the gripping system 51 moves in the horizontal direction towards the clamping device 60.

The clamping means 61 are pivotably mounted in such a manner that the clamping means 61 pivot upon insertion of the conically shaped end regions 25 and subsequently pivot back again in order to clamp the specimen holder 20 in the clamping device 60. Subsequent to this, the measurement is carried out on the specimen. Following termination of the measurement, the gripping system 51 grips the specimen holder 20 by its pegs 24 and removes it from the clamping device 60. Finally, the gripping system 51 feeds the specimen holder 20 to the mounting device 30 again.

The specimen holder 20 according to the invention makes it possible to automatically successively place specimens of different geometries and load types (tensile, compressive, bending, shear) into the test unit 70, to measure them and to remove them again. Manual cleaning of the specimen holders 20, or a modification of the specimen holders 20, is not necessary.

LIST OF REFERENCE SIGNS

10 Specimen holder magazine
11 Carrier stand
20a Specimen holder for compressive test
20b Specimen holder for tensile test
20c Specimen holder for shear test
20d Specimen holder for bending test
21a Specimen mounting device for compressive test
21b Specimen mounting device for tensile test
21c Specimen mounting device for shear test
21d Specimen mounting device for bending test
22 Holding means
23 Specimen
24 Peg
25 Conically shaped end region
26 Mounting plate
27 Transitional region
28 Plate
29 Clamping jaw
46 Holder
47 Clamping jaw
48 Constrictions
49 Bearing
50 Stamp
51 Support plate 52 Spring
53 Recess
30 Mounting device
31 First mounting angle
32 Second mounting angle
33 First leg
34 Second leg
35 Recess
36 End side
37 Oblong section
38 Circular section
39 Outside
40 First depression
41 Second depression
42 Opening
43 Inside
44 Incline
45 End face
50 Specimen feed system
51 Gripping system
52 Gripping pliers
60 Clamping device
61 Clamping means
70 Test unit
L Longitudinal axis

The invention claimed is:

1. A test unit comprising:
   at least one specimen holder for mounting a specimen, the specimen holder including a specimen mounting device for clamping the specimen, a holding means being assigned to said specimen mounting device, said holding means having at least two pegs, which protrude from the specimen mounting device; and
   a specimen feed system for feeding specimen holders to the test unit, wherein the specimen feed system comprises a gripping system which grips the specimen holder on the holding means and feeds the specimen holder to the test unit.

2. The test unit as claimed in claim 1, wherein the pegs have an approximately conically shaped end region.

3. The test unit as claimed in claim 1, wherein the pegs of the specimen holder protrude perpendicularly from opposite sides of the specimen mounting device.

4. The test unit as claimed in claim 1, further comprising a mounting device, for mounting the holding means of the specimen holder.

5. The test unit as claimed in claim 4, wherein the mounting device has a first mounting angle and a second mounting angle, each mounting angle having an approximately L-shaped cross section with a first leg and a second leg.

6. The test unit as claimed in claim 5, wherein a recess is formed into each of the first legs of the mounting angles.

7. The test unit as claimed in claim 6, wherein the recesses are surrounded by a first depression.

8. The test unit as claimed in claim 7, wherein the first mounting angle has a second depression which is formed into the first depression.

9. The test unit as claimed in claim 4, 1 wherein the specimen feed system includes a specimen holder magazine having a carrier stand to which the mounting device for the specimen holder is fastenable.

10. The test unit as claimed in claim 1, wherein the gripping system has two gripping pliers at a distance from one another which grip the holding means of the specimen holder.

11. The test unit as claimed in claim 1, wherein the gripping system is pivotable about its longitudinal axis.

12. A specimen holder for the test unit as claimed in claim 1.

13. The test unit as claimed in claim 1, wherein the at least one specimen holder comprises a plurality of specimen holders including at least two types of specimen holders chosen from a specimen holder for a compression test, a specimen holder for a tensile test, a specimen holder for a shear test, or a specimen holder for a bending test.

* * * * *